US00PP13847P29

(12) United States Plant Patent
Westhoff

(10) Patent No.: US PP13,847 P2
(45) Date of Patent: May 27, 2003

(54) VARIETY OF VERBENA PLANT NAMED 'WESVERDARK'

(75) Inventor: Heinrich Westhoff, Fresenhorst 22-24, 46354 Südlohn/Oeding (DE)

(73) Assignees: Heinrich Westhoff (DE); Josef Westhoff (DE)

( * ) Notice: Subject to any disclaimer, the term of this patent is extended or adjusted under 35 U.S.C. 154(b) by 0 days.

(21) Appl. No.: 10/101,256

(22) Filed: Mar. 19, 2002

(51) Int. Cl.[7] ..... A01H 5/00
(52) U.S. Cl. ..... Plt./308
(58) Field of Search ..... Plt./308

*Primary Examiner*—Kent Bell
(74) *Attorney, Agent, or Firm*—Webb Ziesenheim Logsdon Orkin & Hanson, P.C.

(57) ABSTRACT

A new and distinct early flowering Verbena plant with large, dark red colored flowers with a bright eye and dark green foliage. The plant is suitable for growth in pots and hanging baskets.

1 Drawing Sheet

VARIETAL DENOMINATION

'Wesverdark'.

CLASSIFICATION

*Verbena×hybrida.*

BACKGROUND OF THE INVENTION

The present invention comprises a new and distinct cultivar of Verbena plant known by the varietal name 'Wesverdark'. The new variety was discovered in 1999 in a selected breeding program in Südlohn, Germany designed to produce new colored hanging Verbena. The new variety is a selection from the cross of proprietary unpatented breeding plants named 98 P9 FAT (female) and 98 P10 FAQ (male). The growth character of the new variety is similar to its parents but with different flower color. The new variety was first asexually reproduced in February 1999 by cuttings in Südlohn, Germany. The new variety has been trial and field tested at Südlohn and has been found to retain its distinctive characteristics and remain true to type through successive propagations.

The following traits in combination distinguish 'Wesverdark' as a new and distinct cultivar:

1. Dark red colored flower with a bright eye.
2. Large, solitary flowers.
3. Large and ball-like inflorescence.
4. Compact inflorescence.
5. Many flowers of inflorescence.
6. Dark green leaf color.
7. Very good appearance at a distance.

DESCRIPTION OF THE DRAWINGS

The accompanying photographic drawing depicts an up close view of a typical inflorescence and foliage of the new variety, with the color being as nearly true as is possible with color illustrations of this type.

DESCRIPTION OF THE PLANT

The following detailed description sets forth characteristics of the new cultivar. The data which defines these characteristics were collected by asexual reproductions via terminal cutting and tissue culture carried out in Südlohn, Germany. Plants for the description were 20 weeks old, grown in 12 cm pots and baskets in a greenhouse at 20–25° C. daytime temperature and 16–18° C. night temperature with light levels of 3,000–50,000 lux. The color readings were taken on a plant outdoors and in a greenhouse under natural light. Color references are primarily to The R.H.S. Colour Chart of The Royal Horticultural Society of London.

'Wesverdark' compares to 'A Temari Scarlet' (unpatented) as follows:

TABLE 1

| Similarities | Differences |
|---|---|
| Plant length, plant height | Flower color of 'Wesverdark' is darker red |
| Flower form | Flower diameter of 'Wesverdark' is bigger |
| Stem color, internode length | 'Wesverdark' has more flowers per axil, inflorescence |

'Wesverdark' compares to 'B Tucana Red' (unpatented) as follows:

TABLE 2

| Similarities | Differences |
|---|---|
| Plant length | Flower color of 'Wesverdark' is darker red |
| Branch diameter | Solitary flowers of 'Wesverdark' have a bigger diameter |
| Leaf form | Inflorescence axil of 'Wesverdark' is shorter<br>Leaves of 'Wesverdark' are bigger |

PLANT

Form: Spreading.
Height: 26 cm from soil to top of flowers; 58–90 cm wide.
Time to produce finished flowering plant from rooted cutting: About 3 months in a 12 cm container.
Growth: Vigorous.
Branching habit: Well-branched; freely branching at nearly every node; pinching of terminal apex stimulates development of lateral branches.

Roots:
*Habit.*—Vigorous, fine, well-branched.
*Time to initiate roots.*—About 10 days at 18° C.
*Time to develop roots.*—About 21 days at 18° C.
Lateral branches:
*Color.*—146A and 146B.
*Texture.*—Pubescent.
*Cross sectional shape.*—Tetragonal.
*Length.*—26 cm.
*Diameter.*—Main branches: 3 mm. Lateral branches: 1.9 mm.
*Internode length.*—3.65 cm.
Foliage:
*Arrangement.*—Decussate; simple.
*Persistence.*—Durable, very persistent.
*Size of leaf.*—Length: Base: 8.6 cm. Middle: 5.7 cm. Width: Base: 3.2 cm. Middle: 2.6 cm.
*Shape of leaf.*—Lanceolate.
*Shape of apex.*—Rounded.
*Shape of base.*—Attenuate.
*Texture.*—Leathery; pubescent (short, dense, hard).
*Aspect.*—Flat.
*Margin type.*—Crenate.
*Color.*—Young leaves: Upper surface: 147A. Lower surface: 147B. Mature leaves: Upper surface: 147A. Lower surface: 147B.
*Petioles.*—Length: 7.3 mm. Diameter: 1.9 mm. Color: 147C.
*Veins.*—Venation type: Pinnate. Color: Upper surface: 147A. Lower surface: 147C.

FLOWER

Bud:
*Shape.*—Young: Spherical on the tube of sepals. Before opening: Spherical is slightly opened.
*Diameter.*—Young: 2 mm. Before opening: 2.5 mm.
*Length.*—Young: 1.3 cm. Before opening: 2.1 cm.
*Color.*—Tip: 46A. Middle: 145C. Base: 146B.
Natural flowering season: Spring through Autumn.
Flower type and habit: Salverform flowers arranged on terminal spikes (axiallary corymbs); solitary flowers have a five lobed corolla; freely and continuously flowering; numerous flowers open simultaneously.
Spike:
*Number of flowers per spike.*—34 solitary flowers per spike.
*Length.*—Inflorescence: 3.5 cm. Pedicel: 0.9 cm.
*Diameter.*—Inflorescence: 6 cm. Pedicel: 1.2 mm.
*Pedicel color.*—144B.
*Blooming flowers per spike.*—10–19.
Corolla:
*Form.*—Fused flat salverform; sessil on terminal spikes.
*Fused petals* (*lobed*).—5-lobed corolla.
Solitary flower diameter:
*Horizontal.*—5.5 mm.
*Vertical.*—3.8 mm.
Petals/lobes:
*Number.*—5.
*Length.*—0.9 cm.
*Width.*—0.9 cm.
*Shape.*—Broad obcordate.
*Aspect.*—Flat and face upward.
*Margin.*—Entire; tip emarginate.
*Texture and appearance.*—Smooth, velvety.
*Color when just opening.*—Upper surface: 46A. Lower surface: 53B with 69D.
*Color when fully opened.*—Upper surface: 46A. Lower surface: 53B.
*Circumorbital ring.*—77C.
*Below circumorbital ring.*—145D.
Eye:
*Size.*—4 mm.
*Color.*—145C with dense pubescence.
*Pubescence.*—Dense.
Throat:
*Color.*—145C.
*Texture.*—Pubescent.
*Diameter.*—Top: 2.3 mm. Base: 2 mm.
Tube color: 145C.
Calyx:
*Form.*—Fused (gamopetalous) flat, lobed.
*Length.*—2 cm.
*Sepal shape.*—Fused to a tube; star-shaped cross section.
*Sepal margin.*—Fused.
*Sepal texture.*—Velvety; viscid.
*Sepal color.*—Upper surface (outside): Yellow-Green Group 146B. Lower surface (inside): Yellow-Green Group 146B.
Temperature tolerance: 2–30° C.
Lasting quality: Long-lasting.
Fragrance: None.

REPRODUCTIVE ORGANS

Stamens:
*Number per flower.*—4; didynamous; included, adnate to petals.
*Filament length.*—1 mm.
*Anthers.*—Shape: Two parted; ovate enclosed. Length: 1.5 mm. Width: 1.5 mm. Color: 144B and 144C.
*Pollen.*—Color: 4A. Amount: Slight.
Pistil:
*Number.*—One.
*Length.*—2.1 cm.
*Styles.*—One with superior ovary. Length: 1.7 cm. Color: 145D.
*Stigma.*—Shape: Ovate. Color: Young: 143A. Mature: 144A.
Seeds: Few produced.
Disease/pest resistance: No susceptibility to diseases or pests has been noted to date.

I claim:

1. A new and distinct variety of Verbena plant substantially as shown and described.

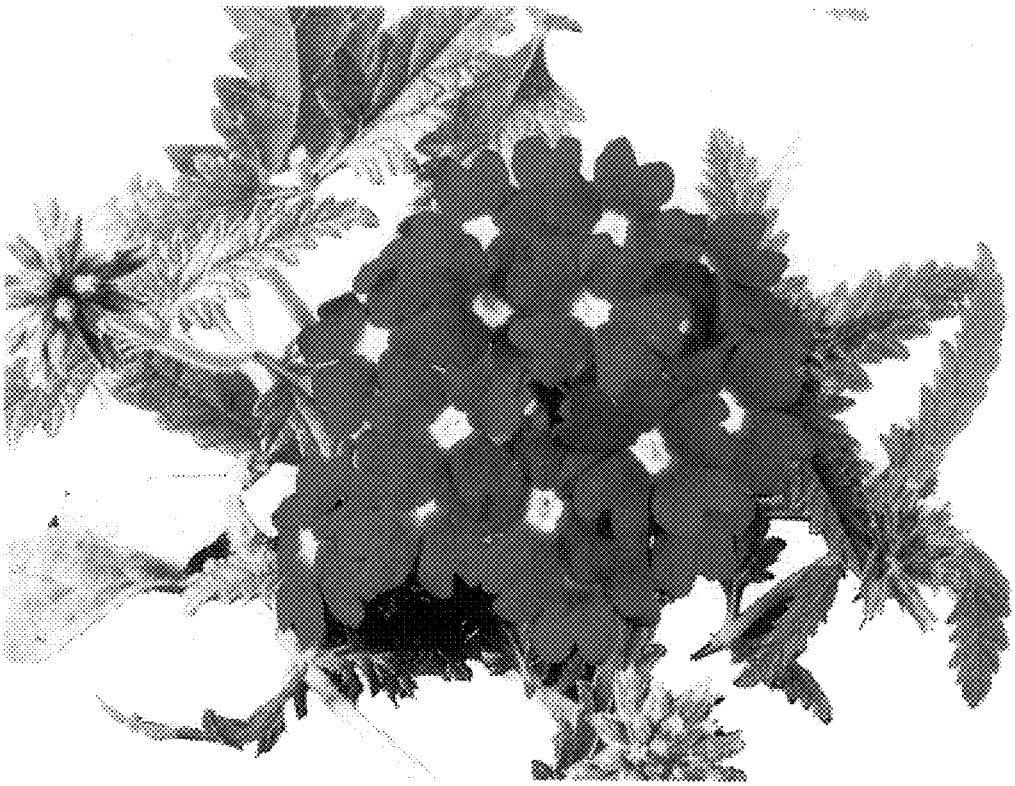

* * * * *